(12) United States Patent
Knutson et al.

(10) Patent No.: US 12,144,602 B2
(45) Date of Patent: Nov. 19, 2024

(54) SIX DEGREES OF FREEDOM FROM A SINGLE INDUCTIVE PICKUP COIL SENSOR

(71) Applicant: Covidien LP, Mansfield, MA (US)

(72) Inventors: Nathan J. Knutson, Long Lake, MN (US); Evan M. Gustafson, Minneapolis, MN (US)

(73) Assignee: Covidien LP, Mansfield, MA (US)

( * ) Notice: Subject to any disclaimer, the term of this patent is extended or adjusted under 35 U.S.C. 154(b) by 383 days.

(21) Appl. No.: 17/585,289

(22) Filed: Jan. 26, 2022

(65) Prior Publication Data

US 2022/0273189 A1 Sep. 1, 2022

Related U.S. Application Data

(60) Provisional application No. 63/154,407, filed on Feb. 26, 2021.

(51) Int. Cl.
| | |
|---|---|
| *A61B 5/06* | (2006.01) |
| *A61B 10/04* | (2006.01) |
| *A61B 34/00* | (2016.01) |
| *A61B 34/20* | (2016.01) |
| *A61B 34/30* | (2016.01) |
| *A61M 25/01* | (2006.01) |

(52) U.S. Cl.
CPC .............. *A61B 5/062* (2013.01); *A61B 10/04* (2013.01); *A61B 34/71* (2016.02); *A61B 2034/2061* (2016.02); *A61B 2034/301* (2016.02); *A61M 25/0147* (2013.01)

(58) Field of Classification Search
CPC .............. A61B 10/04; A61B 2034/107; A61B 2034/2051; A61B 2034/2061; A61B 2034/301; A61B 2034/742; A61B 2090/3762; A61B 2090/3764; A61B 34/10; A61B 34/25; A61B 34/30; A61B 34/71; A61B 5/062; A61M 2025/0166; A61M 25/0147
See application file for complete search history.

(56) References Cited

U.S. PATENT DOCUMENTS

| | | | |
|---|---|---|---|
| 9,039,608 B2 | 5/2015 | Donhowe et al. | |
| 9,918,682 B2 | 3/2018 | Nakada et al. | |
| 2005/0245814 A1 | 11/2005 | Anderson et al. | |
| 2014/0275988 A1 | 9/2014 | Walker et al. | |
| 2016/0228032 A1 | 8/2016 | Walker et al. | |
| 2016/0302873 A1 | 10/2016 | Donhowe et al. | |
| 2017/0007345 A1 | 1/2017 | Smith et al. | |
| 2017/0151027 A1 | 6/2017 | Walker et al. | |
| 2019/0125164 A1 | 5/2019 | Roelle et al. | |
| 2019/0183587 A1 | 6/2019 | Rafii-Tari et al. | |
| 2020/0069218 A1 | 3/2020 | Gliner et al. | |

FOREIGN PATENT DOCUMENTS

CN 212522006 U 2/2021

OTHER PUBLICATIONS

PCT Search Report and Written Opinion issued in PCT/US2022/017535 dated Jun. 17, 2022.

*Primary Examiner* — Michael T Rozanski
(74) *Attorney, Agent, or Firm* — Weber Rosselli & Cannon LLP

(57) ABSTRACT

A method and system of detecting a position and orientation of the catheter in five degrees of freedom (5DOF) in a first position and in a second position and calculating a sixth degree of freedom of the catheter based on a difference in the detected 5DOF position and orientation of the catheter in the first position and the detected 5DOF position and orientation in the second position.

20 Claims, 7 Drawing Sheets

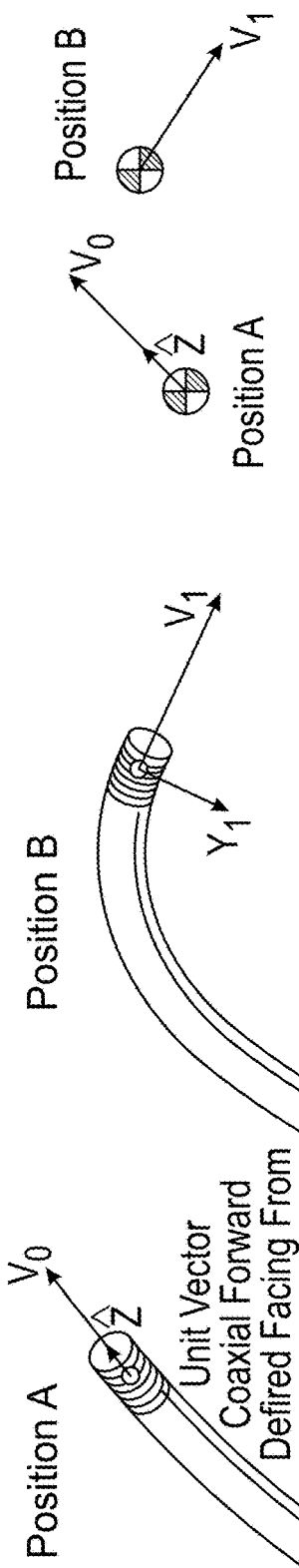

SIX DEGREES OF FREEDOM FROM A SINGLE INDUCTIVE PICKUP COIL SENSOR

CROSS-REFERENCE TO RELATED APPLICATION

This application claims the benefit of, and priority to, U.S. Provisional Patent Application Ser. No. 63/154,407, filed on Feb. 26, 2021, the entire content of which is hereby incorporated by reference herein.

BACKGROUND

Technical Field

This disclosure relates to the field of catheter navigation of and to determining the position and orientation of a distal portion of the catheter.

Description of Related Art

There are several commonly applied medical methods, such as endoscopic procedures or minimally invasive procedures, for treating various maladies affecting organs including the liver, brain, heart, lungs, gall bladder, kidneys, and bones. Often, one or more imaging modalities, such as magnetic resonance imaging (MRI), ultrasound imaging, computed tomography (CT), or fluoroscopy are employed by clinicians to identify and navigate to areas of interest within a patient and ultimately a target for biopsy or treatment. In some procedures, pre-operative scans may be utilized for target identification and intraoperative guidance. However, real-time imaging may be required to obtain a more accurate and current image of the target area. Furthermore, real-time image data displaying the current location of a medical device with respect to the target and its surroundings may be needed to navigate the medical device to the target in a safe and accurate manner (e.g., without causing damage to other organs or tissue).

For example, an endoscopic approach has proven useful in navigating to areas of interest within a patient, and particularly so for areas within luminal networks of the body such as the lungs. To enable the endoscopic approach, and more particularly the bronchoscopic approach in the lungs, endobronchial navigation systems have been developed that use previously acquired MM data or CT image data to generate a three-dimensional (3D) rendering, model, or volume of the particular body part such as the lungs.

The resulting volume generated from the MRI scan or CT scan may be utilized to create a navigation plan to facilitate the advancement of a navigation catheter (or other suitable medical device) through a bronchoscope and a branch of the bronchus of a patient to an area of interest. A locating or tracking system, such as an electromagnetic (EM) tracking system, may be utilized in conjunction with, for example, CT data, to facilitate guidance of the navigation catheter through the branch of the bronchus to the area of interest. In certain instances, the navigation catheter may be positioned within one of the airways of the branched luminal networks adjacent to, or within, the area of interest to provide access for one or more medical instruments.

Accurate determination of position and orientation of the distal portion of the catheter is important to ensure that tools such as biopsy and treatment tools interact with the desired tissue. Improvements to current navigation catheter systems are desired.

SUMMARY

One aspect of the disclosure is directed to a catheter navigation system including: a flexible catheter configured for navigation within a patient, the catheter including a five degrees of freedom (5DOF) sensor; a drive mechanism including at least one pull wire configured to change the position and orientation of the flexible catheter; a computing device configured to detect the 5DOF position and orientation of the sensor, the computing device including a memory and a processor, the memory storing thereon a computer program that when executed by the processor cause the computing device to perform steps of: detecting the position and orientation of the catheter in 5DOF at a first position; signaling the drive mechanism to move the catheter; detecting the position and orientation of the catheter in 5DOF at a second position. The catheter navigation system also includes calculating the roll of the catheter at the second position, where the roll calculation resolves the position and orientation of a distal portion of the catheter in six degrees of freedom (6DOF). Other embodiments of this aspect include corresponding computer systems, apparatus, and computer programs recorded on one or more computer storage devices, each configured to perform the actions of the methods and systems described herein.

Implementations of this aspect of the disclosure may include one or more of the following features. The catheter navigation system where the catheter includes a lumen therethrough for insertion of a biopsy or treatment tool. The catheter navigation system where the drive mechanism causes the catheter to articulate. The catheter navigation system where the drive mechanism causes the catheter to rotate. The catheter navigation system where the catheter includes a curve. The catheter navigation system where the computing device is configured to display a user interface, the user interface depicting the 6DOF position and orientation of the catheter in relation to a target. The catheter navigation system further including a 5DOF electromagnetic sensor to detect the position and orientation of the catheter in 5DOF at the first position and the second position. The catheter navigation system further including a 5DOF shape sensor to detect the position and orientation of the catheter in 5DOF at the first position and the second position. The catheter navigation system further including a fluoroscope, where the fluoroscope is configured for confirming the position of the catheter. The catheter navigation system where signaling the drive mechanism to move the catheter occurs at a frequency between 3 Hz and 10 Hz. Implementations of the described techniques may include hardware, a method or process, or computer software on a computer-accessible medium, including software, firmware, hardware, or a combination of them installed on the system that in operation causes or cause the system to perform the actions. One or more computer programs can be configured to perform particular operations or actions by virtue of including instructions that, when executed by data processing apparatus, cause the apparatus to perform the actions.

A further aspect of the disclosure is directed to a method for detecting the position and orientation of a catheter in six degrees of freedom (6DOF), the method including: detecting a position and orientation of a catheter in five degrees of freedom (5DOF) in a first position; signaling a drive mechanism to move the catheter; detecting a position and orientation of the catheter in 5DOF in a second position; calculating the roll of the catheter based on a difference in the detected 5DOF position and orientation of the catheter in the first position and the detected 5DOF position and orientation in the second position. Other embodiments of this aspect include corresponding computer systems, apparatus, and computer programs recorded on one or more computer storage devices, each configured to perform the actions of the methods and systems described herein.

Implementations of this aspect of the disclosure may include one or more of the following features. The method further including articulating the catheter with a drive mechanism. The method further including rotating the catheter, where the catheter is curved. The method where the position of the catheter is detected via an electromagnetic sensor positioned in a distal portion of the catheter. The method where the position of the catheter is detected via a shape sensor positioned in a distal portion of the catheter. The method further including displaying on a computing device a user interface, the user interface depicting the 6DOF position and orientation of the catheter in relation to a target. The method where signaling the drive mechanism to move the catheter occurs at a frequency between 3 Hz and 10 Hz.

Implementations of the described techniques may include hardware, a method or process, or computer software on a computer-accessible medium, including software, firmware, hardware, or a combination of them installed on the system that in operation causes or cause the system to perform the actions. One or more computer programs can be configured to perform particular operations or actions by virtue of including instructions that, when executed by data processing apparatus, cause the apparatus to perform the actions.

One aspect of the disclosure is directed to a method for detecting the position and orientation of a catheter in six degrees of freedom (6DOF), the method including: detecting X, Y, Z, pitch and yaw position and orientation of a sensor on a distal portion of a catheter at a first position; detecting X, Y, Z, pitch and yaw position and orientation of the sensor on a distal portion of a catheter at a second position; calculating a roll orientation of the sensor at the second position based on the change in x, y, z, pitch, and yaw position and orientation from the first position to the second position. Other embodiments of this aspect include corresponding computer systems, apparatus, and computer programs recorded on one or more computer storage devices, each configured to perform the actions of the methods and systems described herein.

Implementations of this aspect of the disclosure may include one or more of the following features. The method where a pull wire moves the catheter from the first position to the second position. The method where a drive mechanism operating at between 3 Hz and 10 Hz actuates the pull wire to move the catheter from the first position to the second position.

BRIEF DESCRIPTION OF THE DRAWINGS

Various aspects and embodiments of the disclosure are described hereinbelow with references to the drawings, wherein:

FIG. 6A depicts a catheter with 5DOF sensor and pull wire in an unarticulated state in accordance with the disclosure;

FIG. 6B depicts a catheter with 5DOF sensor and pull wire in an unarticulated state in accordance with the disclosure;

FIG. 6C depicts the change in vector associated with the articulation of the catheter from FIG. 6A to FIG. 6B; and FIG. 6D depicts the articulation plane defined by the articulation of the catheter from FIG. 6A to FIG. 6B and a vector normal to the plane to determine the roll of the catheter.

DETAILED DESCRIPTION

Figure 1:
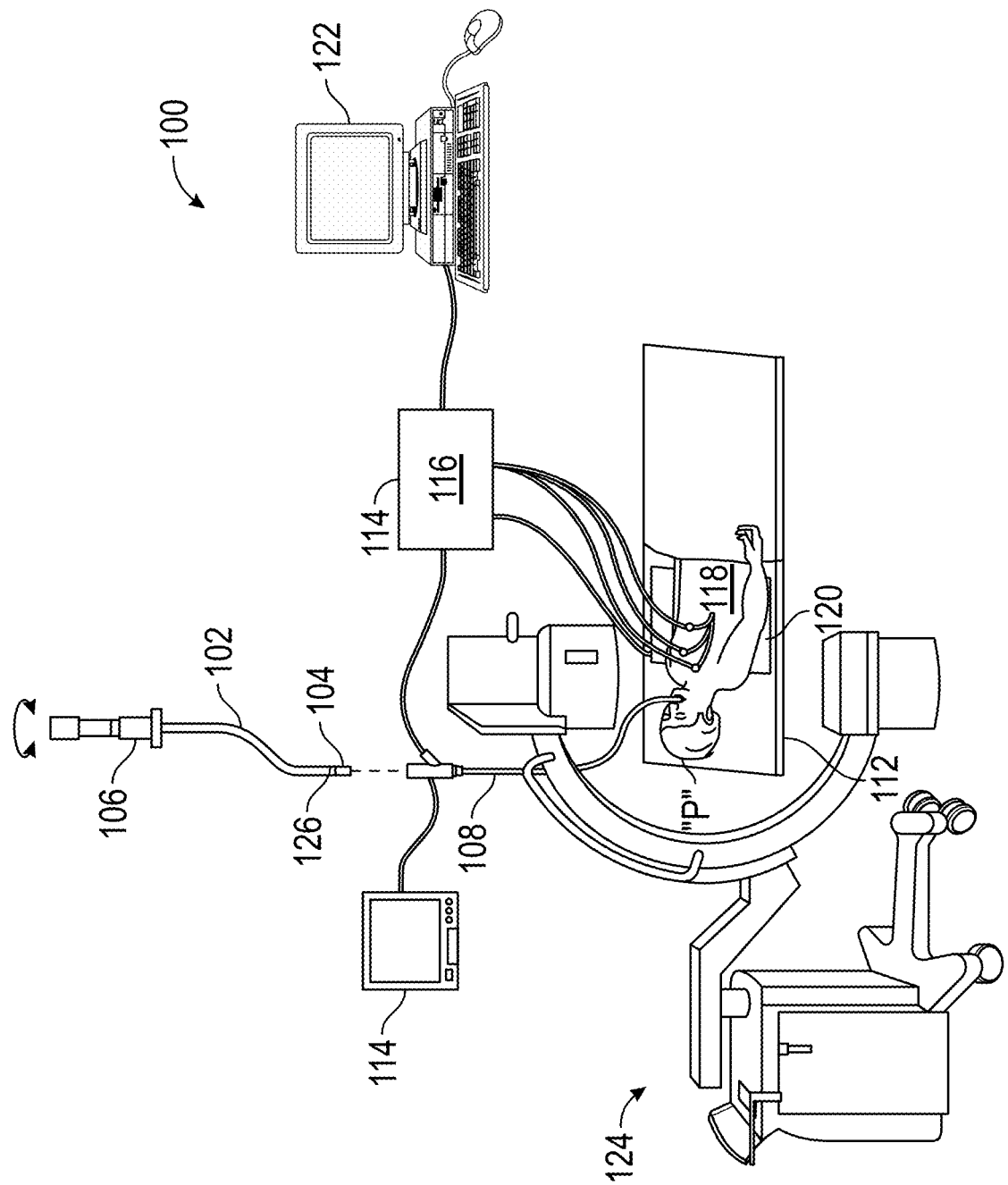
FIG. 1 is a schematic diagram of a system for navigating to soft-tissue targets via luminal networks in accordance with the disclosure.

This disclosure is directed to determining the position and orientation of a catheter within the body of a patient. In particular the disclosure is directed to determining the position and orientation of the distal portion of the catheter in six degrees of freedom (6DOF) utilizing a sensor which renders the position and orientation of the distal portion of the catheter in five degrees of freedom (5DOF). Said another way the disclosure is directed to determining the X, Y, Z coordinates and the pitch, yaw, and, roll orientation of the distal portion of the catheter form sensor output providing only X, Y, Z, pitch, and yaw position and orientation data. In large part the systems and methods described herein utilize detected movement or change in position of the distal portion of the catheter, given the expected input, to calculate the missing roll information (i.e. the roll DOF data).

In accordance with the disclosure, a 3D volume of a patient's lungs or another suitable portion of the anatomy, may be generated from previously acquired scans, such as CT scans. These scans may be used to generate a 3D model of the anatomy. The 3D model and related scan data are used to identify targets, e.g., potential lesions for biopsy or treatment, and to generate a pathway plan through the anatomy to reach the targets.

Once the pathway plan is generated and accepted by a clinician, that pathway plan may be utilized by a navigation system to drive a catheter along the pathway plan through the anatomy to reach the desired target. The driving of the catheter along the pathway plan may be manual or it may be robotic, or a combination of both. Manual systems include the ILLUMISITE navigation system sold by Medtronic PLC, robotic systems include the ION system sold by Intuitive Surgical Inc. and the MONARCH system sold by Auris Health, Inc. In a single procedure planning, registration of the pathway plan to the patient, and navigation are performed to enable a medical device, e.g., a catheter to be navigated along the planned path to reach a target, e.g., a lesion, so that a biopsy or treatment of the target can be completed.

As noted above, whether manual or robotic, the pathway plan and 3D model developed from the pre-procedure scan data may be registered to the patient before navigation of the catheter to a target within the anatomy can being. Once registered, a catheter or other tool may be navigated following the pathway plan to a desired location. Alternatively, the registration may occur as part of the navigation procedure where landmarks and other features (e.g., carina) and visual feedback using a camera are identified to collect sufficient data to generate a registration of the 3D model to the patient. While this registration is generally more that suitable for general navigation of the pathway, regardless of the registration method employed, and there are numerous registration methods, the 3D model and pathway plan may still not provide sufficient accuracy for target interaction allowing for the guidance of medical devices or instruments into the target for biopsy and treatment.

In some cases, the inaccuracy is caused by deformation of the patient's lungs during the procedure relative to the lungs at the time of the acquisition of the previously acquired CT data. This deformation (CT-to-Body divergence) may be caused by many different factors including, for example, changes in the body when transitioning from between a sedated state and a non-sedated state, the bronchoscope changing the patient's pose, the bronchoscope and catheter pushing the tissue, different lung volumes (e.g., the CT scans are acquired during full breath hold following inhale while navigation is typically performed while the patient is breathing), different beds, different days, etc. Thus, another imaging modality may be employed to assist in visualizing medical devices and targets in real-time and enhance the in-vivo navigation procedure.

In navigating the medical device to the target, clinicians may use a fluoroscopic imaging to visualize the position of the medical device relative to the target. While fluoroscopic images show highly dense objects, such as metal tools, bones, and large soft-tissue objects, e.g., the heart, the fluoroscopic images may not clearly show small soft-tissue objects of interest, such as lesions. Furthermore, the fluoroscopic images are two-dimensional (2D) projections which makes determining depths in the view difficult.

X-ray volumetric reconstruction has been developed to enable identification of soft tissue objects and to update the relative position of the target and the catheter in the pathway plan and 3D model. The volumetric reconstruction is made from a series of 2D fluoroscopic images taken at different angles to the tissue in question. In one method described in greater detail below, updating of the pathway plan and relative positions of the catheter and target can be achieved with a local registration process. This local registration process reduces CT-to-body divergence. After the local registration process, in one embodiment a locatable guide (i.e., a catheter with multiple sensors) may be removed from the catheter and a medical device, e.g., a biopsy tool, is introduced into the catheter for navigation to the target to perform the biopsy or treatment of the target, e.g., the lesion.

However, even with local registration where the relative position of the catheter and the target is updated in the 3D model and the pathway plan, maintaining the alignment of the catheter and the target as confirmed in the local registration can be challenging. The source of this challenge is related to two primary functions of the body, namely respiration and cardiac functions (i.e., heartbeat).

Another source of errors is the passage of tools through the catheter after local registration can cause tip deflection. When the catheter includes a sensor, e.g., an electromagnetic sensor or a flexible sensor (sensing shape and orientation of a portion of the catheter) these types of movements can be reported to the clinician via a graphic user interface (GUI) on which navigation software is displayed and allows for following the pathway plan to the target. Movements caused by the passage of tools through the catheter appear as movement of the target relative the position of the catheter on the GUI.

In accordance with embodiment of the disclosure the catheter 102 includes one or more pull wires. The movement of the sensor is sensed by the navigation system and micro-adjustments can be made to the location of the catheter by manipulating the pull wires. These same pull wires can be employed to constantly adjust the position of the catheter, and specifically the distal portion of the catheter 102 as it moves within the lung. The pull wires cause the catheter 102 to change shape and curvature at the distal portion and may be manipulated either manually by a clinician or automatically via a computer-controlled system (e.g., a robot).

In accordance with aspects of the disclosure, and as noted above, the visualization of intra-body navigation of a medical device, e.g., a biopsy tool, towards a target, e.g., a lesion, may be a portion of a larger workflow of a navigation system, such as an electromagnetic navigation system. FIG. 1 is a perspective view of an exemplary system for facilitating navigation of a medical device, e.g., a catheter to a soft-tissue target via airways of the lungs. Those of skill in the art will recognize that other systems for navigation within a patient whether it be in the gastro-intestinal track (i.e., colon, intestines, stomach, and esophagus), vasculature, navigation within the thoracic and abdominal cavities (e.g., laparoscopic procedures) and others without departing from the scope of the disclosure.

System 100 may be configured to construct fluoroscopic based three-dimensional volumetric data of the target area from 2D fluoroscopic images to confirm navigation to a desired location. System 100 may be further configured to facilitate approach of a medical device to the target area by using Electromagnetic Navigation (EMN) and for determining the location of a medical device with respect to the target. One such EMN system is the ILLUMISITE system currently sold by Medtronic PLC, though other systems for intraluminal navigation are considered within the scope of the disclosure, as noted above.

One aspect of the system 100 is a software component for reviewing of computed tomography (CT) image scan data that has been acquired separately from system 100. The review of the CT image data allows a user to identify one or more targets, plan a pathway to an identified target (planning phase), navigate a catheter 102 to the target (navigation phase) using a user interface on computing device 122, and confirming placement of a sensor 104 relative to the target. The target may be tissue of interest identified by review of the CT image data during the planning phase. Following navigation, a medical device, such as a biopsy tool or other tool, may be inserted into catheter 102 to obtain a tissue sample from the tissue located at, or proximate to, the target.

As shown in FIG. 1, catheter 102 is part of a catheter guide assembly 106. In practice, catheter 102 is inserted into a bronchoscope 108 for access to a luminal network of the patient P. Specifically, catheter 102 of catheter guide assembly 106 may be inserted into a working channel of bronchoscope 108 for navigation through a patient's luminal network. A sensor 104 is located on the distal portion of the catheter 102. The position and orientation of sensor 104 relative to a reference coordinate system, and thus the distal portion of catheter 102, within an electromagnetic field can be derived. Catheter guide assemblies 106 are currently marketed and sold by Medtronic PLC under the brand names SUPERDIMENSION® Procedure Kits, or EDGE™ Procedure Kits, and are contemplated as useable with the disclosure.

System 100 generally includes an operating table 112 configured to support a patient P, a bronchoscope 108 configured for insertion through patient P's mouth into patient P's airways; monitoring equipment 114 coupled to bronchoscope 108 (e.g., a video display, for displaying the video images received from the video imaging system of bronchoscope 108); a locating or tracking system 114 including a locating module 116, a plurality of reference sensors 18 and a transmitter mat 120 including a plurality of incorporated markers; and a computing device 122 including software and/or hardware used to facilitate identification of a target, pathway planning to the target, navigation of a medical device to the target, and/or confirmation and/or determination of placement of catheter 102, or a suitable device therethrough, relative to the target. Computing device 122 may be similar to workstation 401 of FIG. 5 and may be configured to execute the methods of the disclosure including the method of FIG. 4.

A fluoroscopic imaging device 124 capable of acquiring fluoroscopic or x-ray images or video of the patient P is also included in this particular aspect of system 100. The images, sequence of images, or video captured by fluoroscopic imaging device 124 may be stored within fluoroscopic imaging device 124 or transmitted to computing device 122 for storage, processing, and display. Additionally, fluoroscopic imaging device 124 may move relative to the patient P so that images may be acquired from different angles or perspectives relative to patient P to create a sequence of fluoroscopic images, such as a fluoroscopic video. The pose of fluoroscopic imaging device 124 relative to patient P and while capturing the images may be estimated via markers incorporated with the transmitter mat 120. The markers are positioned under patient P, between patient P and operating table 112 and between patient P and a radiation source or a sensing unit of fluoroscopic imaging device 124. The markers incorporated with the transmitter mat 120 may be two separate elements which may be coupled in a fixed manner or alternatively may be manufactured as a single unit. Fluoroscopic imaging device 124 may include a single imaging device or more than one imaging device.

Computing device 122 may be any suitable computing device including a processor and storage medium, wherein the processor is capable of executing instructions stored on the storage medium. Computing device 122 may further include a database configured to store patient data, CT data sets including CT images, fluoroscopic data sets including fluoroscopic images and video, fluoroscopic 3D reconstruction, navigation plans, and any other such data. Although not explicitly illustrated, computing device 122 may include inputs, or may otherwise be configured to receive, CT data sets, fluoroscopic images/video and other data described herein. Additionally, computing device 122 includes a display configured to display graphical user interfaces. Computing device 122 may be connected to one or more networks through which one or more databases may be accessed.

With respect to the planning phase, computing device 122 utilizes previously acquired CT image data for generating and viewing a three-dimensional model or rendering of patient P's airways, enables the identification of a target on the three-dimensional model (automatically, semi-automatically, or manually), and allows for determining a pathway through patient P's airways to tissue located at and around the target. More specifically, CT images acquired from previous CT scans are processed and assembled into a three-dimensional CT volume, which is then utilized to generate a three-dimensional model of patient P's airways. The three-dimensional model may be displayed on a display associated with computing device 122, or in any other suitable fashion. Using computing device 122, various views of the three-dimensional model or enhanced two-dimensional images generated from the three-dimensional model are presented. The enhanced two-dimensional images may possess some three-dimensional capabilities because they are generated from three-dimensional data. The three-dimensional model may be manipulated to facilitate identification of target on the three-dimensional model or two-dimensional images, and selection of a suitable pathway through patient P's airways to access tissue located at the target can be made. Once selected, the pathway plan, three-dimensional model, and images derived therefrom, can be saved and exported to a navigation system for use during the navigation phase(s). The ILLUMISITE software suite currently sold by Medtronic PLC includes one such planning software.

With respect to the navigation phase, a six degrees-of-freedom electromagnetic locating or tracking system 114, or other suitable system for determining position and orientation of a distal portion of the catheter 102, is utilized for performing registration of the images and the pathway for navigation. Tracking system 114 includes the tracking module 116, a plurality of reference sensors 118, and the transmitter mat 120 (including the markers). Tracking system 114 is configured for use with a catheter 102 and particularly sensor 104.

Transmitter mat 120 is positioned beneath patient P. Transmitter mat 120 generates an electromagnetic field around at least a portion of the patient P within which the position of a plurality of reference sensors 118 and the sensor 104 can be determined with use of a tracking module 116. One or more of reference sensors 118 are attached to the chest of the patient P. Registration is generally performed to coordinate locations of the three-dimensional model and two-dimensional images from the planning phase, with the patient P's airways as observed through the bronchoscope 108, and allow for the navigation phase to be undertaken with knowledge of the location of the sensor 104.

Registration of the patient P's location on the transmitter mat 120 may be performed by moving sensor 104 through the airways of the patient P. More specifically, data pertaining to locations of sensor 104, while catheter 102 is moving through the airways, is recorded using transmitter mat 120, reference sensors 118, and tracking system 114. A shape resulting from this location data is compared to an interior geometry of passages of the three-dimensional model generated in the planning phase, and a location correlation between the shape and the three-dimensional model based on the comparison is determined, e.g., utilizing the software on computing device 122. In addition, the software identifies non-tissue space (e.g., air filled cavities) in the three-dimensional model. The software aligns, or registers, an image representing a location of sensor 104 with the three-dimensional model and/or two-dimensional images generated from the three-dimension model, which are based on the recorded location data and an assumption that sensor 104 remains located in non-tissue space in patient P's airways. Alternatively, a manual registration technique may be employed by navigating the bronchoscope 108 with the sensor 104 to pre-specified locations in the lungs of the patient P, and manually correlating the images from the bronchoscope to the model data of the three-dimensional model.

Still a further aspect of the disclosure relates to the catheter 102. The catheter 102 may include one or more pull-wires which can be used to manipulate the distal portion of the catheter. Pull-wire systems are known and used in a variety of settings including manual, power assisted, and robotic surgeries. In most catheter-based pull-wire systems at least one but up to six and even ten pull wires are incorporated into the catheter 102 and extend from proximate the distal end to a drive mechanism located at a proximal end. By tensioning and relaxing the pull-wires the shape of the distal portion of the catheter can be manipulated. For example, in a simple two pull-wire system by relaxing one pull-wire and retracting an opposing pull-wire the catheter may be deflected in the direction of the retracting pull-wire. Though certain pull-wire systems are described here in detail, the disclosure is not so limited, and the manipulation of the catheter 102 may be achieved by a variety of means including concentric tube systems and others that enable movement of the distal end of the catheter 102. Further though a motor assisted/robotic system is described in detail, the same principals of extension and retraction of pull wires may be employed by manual manipulation means to change the shape of the distal portion of the catheter without departing from the scope of the disclosure.

Though described herein with respect to EMN systems using EM sensors, the instant disclosure is not so limited and may be used in conjunction with flexible sensor, ultrasonic sensors, or with other types of sensors. Additionally, the methods described herein may be used in conjunction with robotic systems such that robotic actuators drive the catheter 102 or bronchoscope 108 proximate the target as described in greater detail below.

Figure 2A:
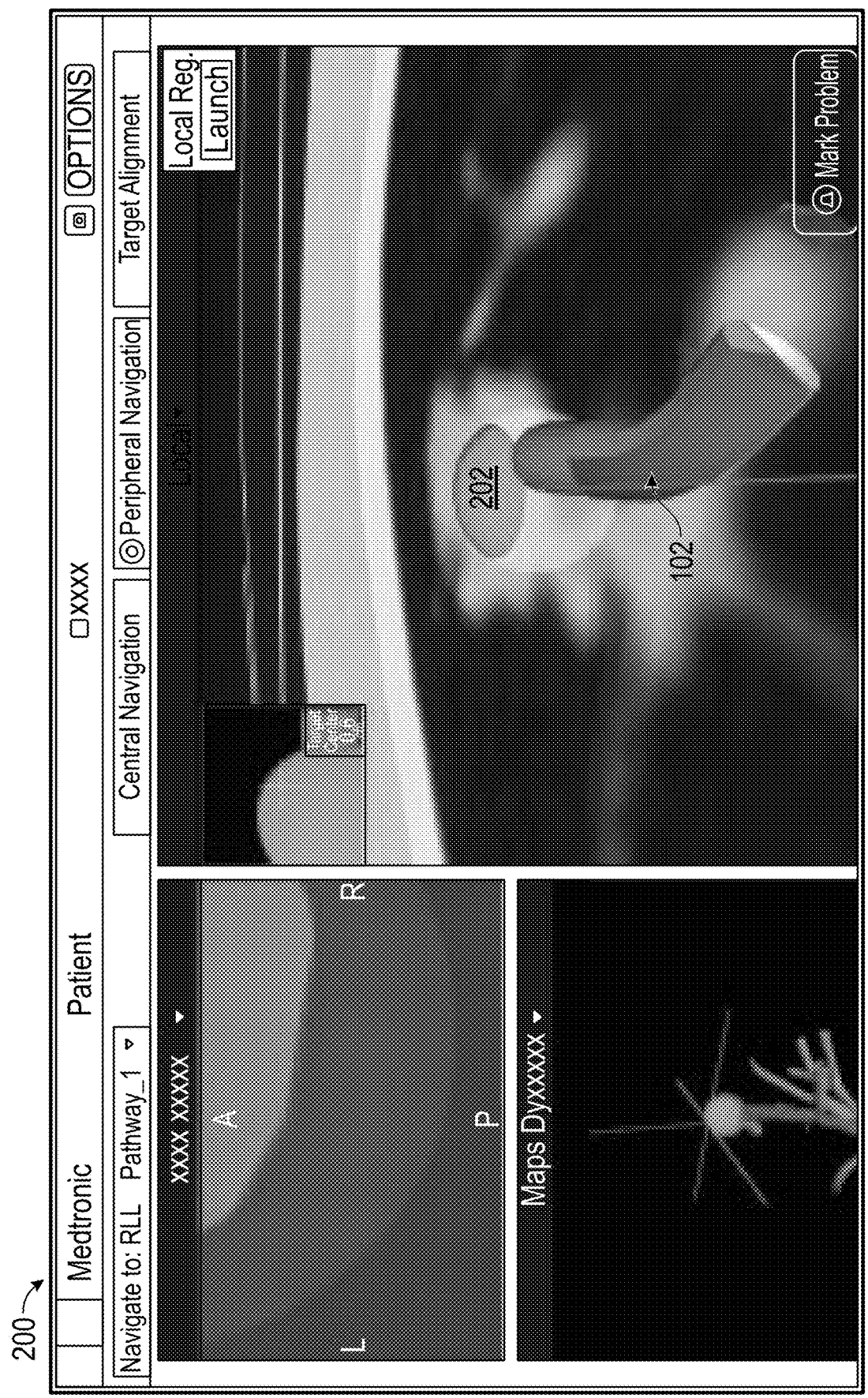
FIG. 2A is a user interface of a navigation program in accordance with aspects of the disclosure.

Following registration of the patient P to the image data and pathway plan, a user interface 200 as shown in FIG. 2A is displayed on the computing device 122 using the navigation software which sets forth the pathway that the clinician is to follow to reach the target. Once catheter 102 has been successfully navigated proximate, as shown in FIG. 2A, the target 202 a local registration process may be performed for each target to reduce the CT-to-body divergence.

Figure 2B:
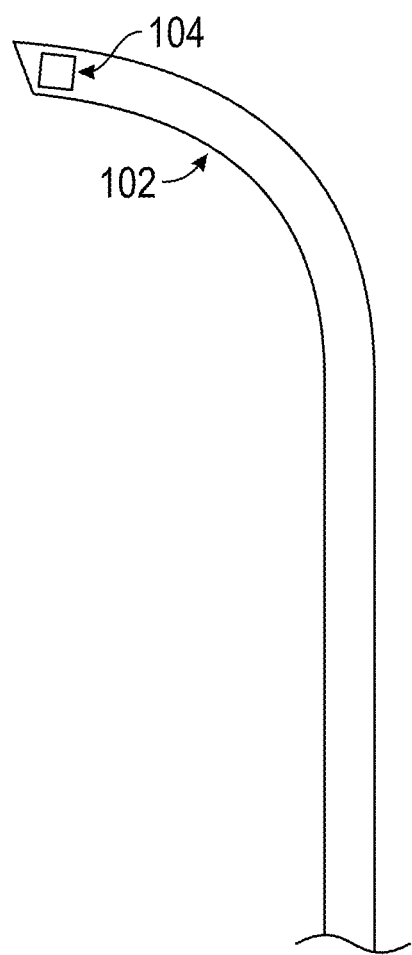
FIG. 2B is a profile view of a curved catheter in accordance with the disclosure.

Though catheter 102 is depicted herein as having a straight configuration, the disclosure is not so limited. Catheter 102 may have a curved shape ranging from a 10-degree to a 180-degree or greater curve. One example is depicted in FIG. 2B, wherein the catheter 102 has a curve of approximately 90 degrees. During navigation, upon arriving at a bifurcation, the curves in the shape of the catheter 102 enable rotation of the catheter 102 such that the distal end of the catheter is aligned with a particular branch through which navigation is intended to proceed. Advancement of the catheter 102 then ensures with the curve so aligned ensures that navigation will continue in the desired branch. Such curves can be particularly useful with navigating the upper lobes of the lungs. As will be described herein below, such curves in the catheter can also be useful in determining the roll of the catheter 102.

In procedures such as lung biopsy and treatment it is useful to ensure that the distal end of the catheter 102 is pointed directly at the target. In accordance with one aspect of the disclosure, the position and orientation of the target is detected and monitored as described above. Further, the position of the catheter 102 may be adjusted by a drive mechanism manipulating the pull-wires to ensure that the catheter always points to the target.

In accordance with the disclosure, the drive mechanism may receive signals derived by the computing device 122 to drive the catheter (e.g., extend and retract pull-wires) based on the observed movement of the catheter 102 and the target caused by respiration and cardiac cycles. One example of such a device can be seen in FIG. 3A which depicts a housing including three drive motors to manipulate a catheter extending therefrom in 5 degrees of freedom (e.g., left right, up, down, and rotation). Other types of drive mechanisms including fewer or more degrees of freedom and other manipulation techniques may be employed without departing from the scope of the disclosure.

As noted above, FIG. 3A depicts a drive mechanism 200 housed in a body 201 and mounted on a bracket 202 which integrally connects to the body 201. The catheter 102 connects to and in one embodiment forms an integrated unit with internal casings 204a and 204b, and connects to a spur gear 206. This integrated unit is, in one embodiment rotatable in relation to the housing 201, such that the catheter 102, internal casings 204 a-b, and spur gear 206 can rotate about shaft axis "z". The catheter 102 and integrated internal casings 204 a-b are supported radially by bearings 208, 210, and 212. Though drive mechanism 200 is described in detail here, other drive mechanisms may be employed to enable a robot or a clinician to drive the catheter to a desired location without departing from the scope of the disclosure.

An electric motor 214R, may include an encoder for converting mechanical motion into electrical signals and providing feedback to the computing device 122. Further, the electric motor 214R (R indicates this motor if for inducing rotation of the catheter 102) may include an optional gear box for increasing or reducing the rotational speed of an attached spur gear 215 mounted on a shaft driven by the electric motor 214R. Electric motors 214LR (LR referring to left-right movement of an articulating portion 217 of the catheter 102) and 214UD (referring to up-down movement of the articulating portion 217), each motor optionally includes an encoder and a gearbox. Respective spur gears 216 and 218 drive up-down and left-right steering cables, as will be described in greater detail below. All three electric motors 214 R, LR, and UD are securely attached to the stationary frame 202, to prevent their rotation and enable the spur gears 215, 216, and 218 to be driven by the electric motors.

Figure 3A:
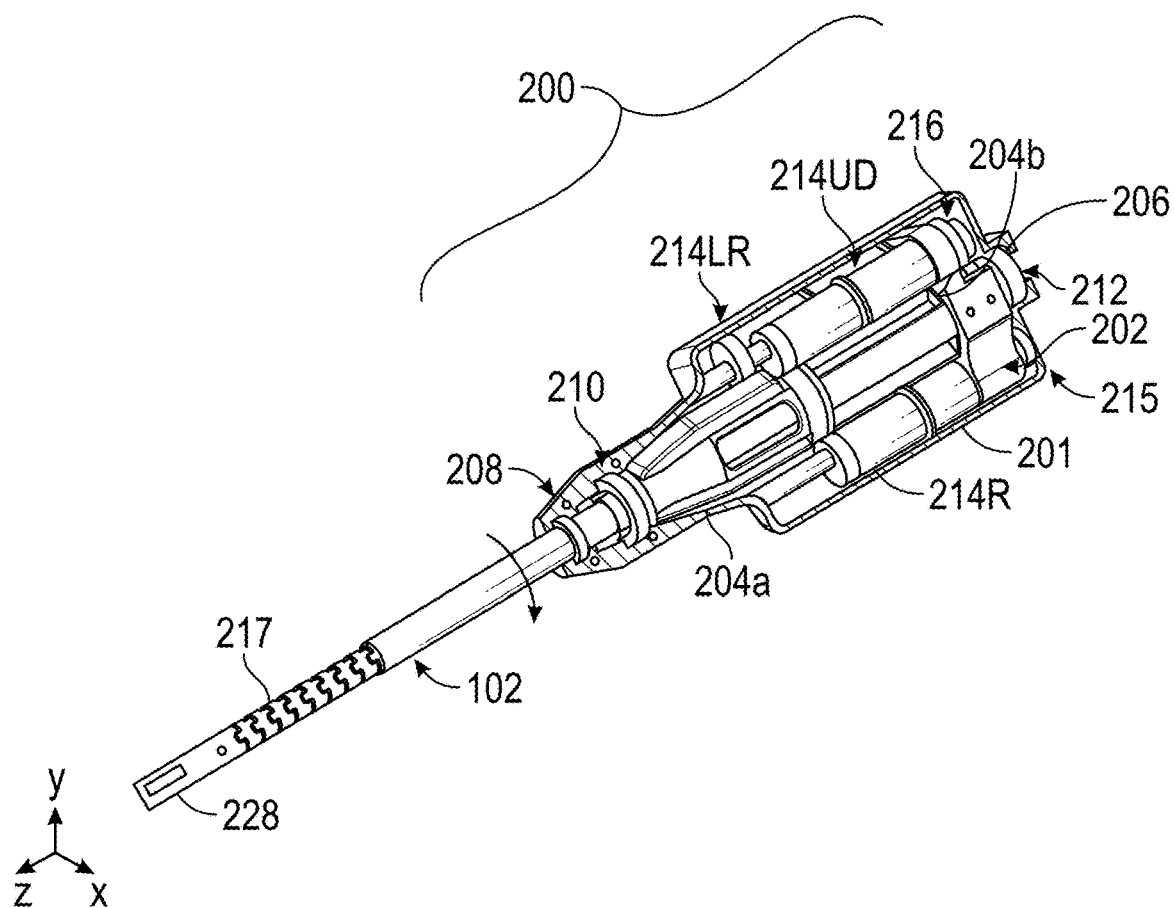
FIG. 3A is a perspective view of a motorized catheter in accordance with the disclosure.
Figure 3B:
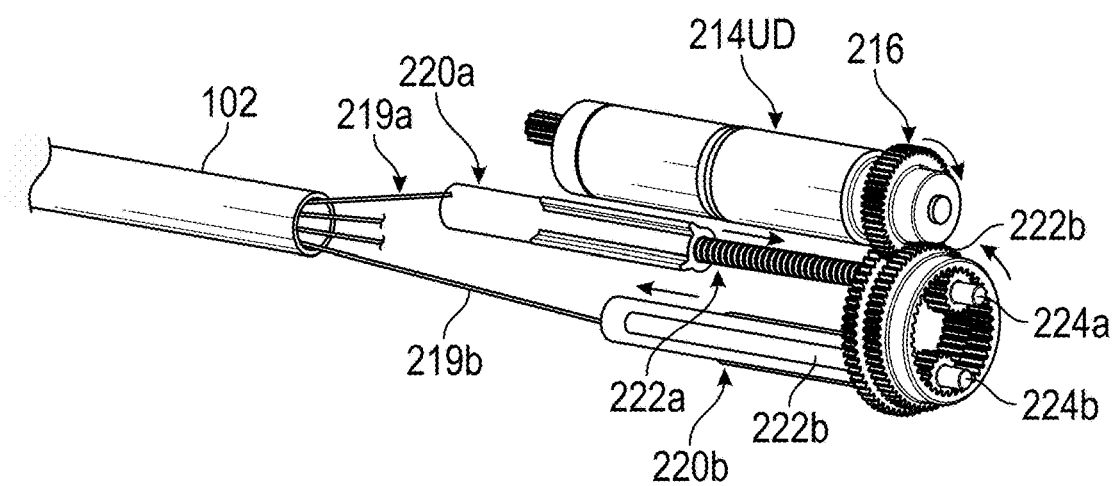
FIG. 3B is a detailed magnified view of a portion of the drive mechanism of the motorized catheter of FIG. 3A.

FIG. 3B depicts details of the mechanism causing articulating portion 217 of catheter 102 to articulate. Specifically, the following depicts the manner in which the up-down articulation is contemplated in one aspect of the disclosure. Such a system alone, coupled with the electric motor 214UD for driving the spur gear 216 would accomplish articulation as described above in a two-wire system. However, where a four-wire system is contemplated, a second system identical to that described immediately hereafter, can be employed to drive the left-right cables. Accordingly, for ease of understanding just one of the systems is described herein, with the understanding that one of skill in the art would readily understand how to employ a second such system in a four-wire system. Those of skill in the art will recognize that other mechanisms can be employed to enable the articulation of a distal portion of a catheter and other articulating catheters may be employed without departing from the scope of the disclosure.

To accomplish up-down articulation of the articulating portion 217 of the catheter 102, steering cables 219a-b may be employed. The distal ends of the steering cables 219a-b are attached to, or at, or near the distal end of the catheter 102. The proximal ends of the steering cables 219a-b are attached to the distal tips of the posts 220a, and 220b. The posts 220a and 220b reciprocate longitudinally, and in opposing directions. Movement of the posts 220a causes one steering cable 219a to lengthen and at the same time, opposing longitudinal movement of post 220b causes cable 219b to effectively shorten. The combined effect of the change in effective length of the steering cables 219a-b is to cause joints a forming the articulating portion 217 of catheter 102 shaft to be compressed on the side in which the cable 219b is shortened, and to elongate on the side in which steering cable 219 a is lengthened.

The opposing posts 220a and 1220b have internal left-handed and right-handed threads, respectively, at least at their proximal ends. Housed within casing 1204b are two threaded shafts 222a and 222b, one is left-hand threaded and one right-hand threaded, to correspond and mate with posts 220a and 220b. The shafts 222a and 222b have distal ends which thread into the interior of posts 220a and 220a and proximal ends with spur gears 224a and 224b. The shafts 222a and 222b have freedom to rotate about their axes. The spur gears 224a and 224b engage the internal teeth of planetary gear 226. The planetary gear 226 also includes external teeth which engage the teeth of spur gear 218 on the proximal end of electric motor 214UD.

To articulate the catheter in the upwards direction, a clinician may activate via an activation switch (not shown) for the electric motor 214UD causing it to rotate the spur gear 218, which in turn drives the planetary gear 226. The planetary gear 226 is connected through the internal gears 224a and 224b to the shafts 222a and 222b. The planetary gear 226 will cause the gears 224a and 224b to rotate in the same direction. The shafts 222a and 222b are threaded, and their rotation is transferred by mating threads formed on the inside of posts 220a and 220b into linear motion of the posts 220a and 220b. However, because the internal threads of post 220a are opposite that of post 220b, one post will travel distally and one will travel proximally (i.e., in opposite directions) upon rotation of the planetary gear 226. Thus, the upper cable 219a is pulled proximally to lift the catheter 102, while the lower cable 219b must be relaxed. As stated above, this same system can be used to control left-right movement of the end effector, using the electric motor 214LR, its spur gear 216, a second planetary gear (not shown), and a second set of threaded shafts 222 and posts 220 and two more steering cables 219. Moreover, by acting in unison, a system employing four steering cables can approximate the movements of the human wrist by having the three electric motors 214 and their associated gearing and steering cables 219 computer controlled by the computing device 122.

Though generally described above with respect to receiving manual inputs from a clinician as might be the case where the drive mechanism is part of a hand-held catheter system, the disclosure is not so limited. In a further embodiment, the drive mechanism 200 is part of a robotic system for navigating the catheter 102 to a desired location within the body. In accordance with this disclosure, in instances where the drive mechanism is part of a robotic catheter drive system, the position of the distal portion of the catheter 102 may be robotically controlled. In such an instance the computing device 122, which determines the position of the target and the catheter 102

The drive mechanism may receive inputs from computing device 122 or another mechanism through which the surgeon specifies the desired action of the catheter 102. Where the clinician controls the movement of the catheter 102, this control may be enabled by a directional button, a joystick such as a thumb operated joystick, a toggle, a pressure sensor, a switch, a trackball, a dial, an optical sensor, and any combination thereof. The computing device responds to the user commands by sending control signals to the motors 214. The encoders of the motors 214 provide feedback to the control unit 24 about the current status of the motors 214.

In a further aspect of the disclosure the catheter 102 may include or be configured to receive an ultrasound imager 228. The ultrasound imager 228 may be a radial ultrasound transducer, a linear ultrasound transducer, a capacitive micromachined ultrasonic transducer, a piezoelectric micromachined ultrasonic transducers, or others without departing from the scope of the disclosure. In accordance with the disclosure, following the navigation of the catheter 102 to a location proximate the target and conducting the local registration, an ultrasound imaging application may be engaged. By conducting the local registration procedure CT-to-body divergence has been eliminated, and the clinician has confidence that the relative position of the catheter 102 and the target as displayed in the navigation software is an accurate representation of the placement of the catheter 102 within the body, relative to the target.

There are a variety of methods of determining the 6DOF position and orientation of the 5DOF sensor 104, and therewith the distal portion of the catheter 102. As noted above, a 5DOF sensor cannot directly provide the data relating to the roll of the catheter 102. A 5DOF sensor is quite beneficial when employed in catheter 102 as it can be constructed from a wire wrapped around an inner portion of the distal end of the catheter 102. Heating and reflowing an outer portion and inner portion of the catheter such that the two portions fuse secures the windings within the catheter 102. This leaves a working channel within the catheter 102 available for the insertion of biopsy and treatment tools such as microwave ablation catheters and others. In contrast, 6DOF sensors typically require elements which prevent a working channel from passing through the catheter 102. However, as noted elsewhere this comes at the cost of the loss of the roll data.

Two options are available for determining the 6th DOF (i.e., the roll) of a catheter 102 as it is navigated through the airways of a patient. In the case of a curved catheter 102 as depicted in FIG. 2B, rotation of the catheter 102 results in a change in position and orientation of the distal portion of the catheter 102 and the 5DOF sensor 104. This change in position and orientation can affect any of the 5DOF, but will certainly cause several of these (e.g., X, Y, Z, pitch, and yaw) to change. The detected change in position and orientation of the 5DOF sensor can be used by an application running computing device 122 or on locating module 116 to estimate the amount of roll necessary to achieve the change in position and orientation. In the case of a motor assisted or robotic system as depicted in FIGS. 3A and 3B, the input to achieve the desired rotation is also known. Thus, where it is known that 10 degrees of roll are input to the catheter 102, the change in position and orientation of the sensor 104 on the curved catheter 102 (e.g., the distal portion of the catheter) can be compared with the determined roll amount. This comparison can be utilized by the application to determine a relative accuracy of the roll calculation. The roll experienced by the catheter 102 can then be updated on the UI 150 of FIG. 2A.

Alternatively, in the case of a straight but articulatable catheter 102, such as those employing the drive mechanism 200 depicted in FIGS. 3A and 3B, the distal portion of the catheter 102 may be articulated. Similar to the curved catheter 102, articulation of catheter 102 can achieve much the same purpose as rotation of the curved catheter 102. Again, the change in position and orientation of the distal portion of the catheter 102, and particularly 5DOF sensor 104 can be used to determine amount of roll (the $6^{th}$ DOF) experienced by the sensor 104 as a result of the articulation and a change in location and orientation of the sensor. In particular, when just a single pull wire or a two pull wire system is employed where articulation in only in a single plane, determination of the plane of the articulation can be employed in combination with the change in position and orientation to calculate the amount of roll which the catheter 102 experiences at any given time.

One of the benefits of the motor assist or robotic system such as drive mechanism 200 is that articulations can be automated as part of the drive process. In this way despite appearing to be a continuous drive to a desired target within the patient, at a frequency of for example, between 3 and 10 hz, the distal portion of the catheter 102 can be regularly articulated. In this manner the roll of the catheter 102 can be continually calculated during the navigation of the catheter 102. The actual frequency of articulation is preferably one at which no other component of the system 100 operates, thus the detection of the articulation can be isolated from other movements of the catheter 102. This determination is assisted by the fact that the system 100 knows the timing of the articulation and can confirm that movement is a result of the articulation. Though not referenced with respect to FIGS. 3A and 3B, a variety of means can be employed to determine the amount of roll or articulation applied to the catheter 102. These means include servo or stepper motor based systems, optical scale systems, where rotations of a marker are observed, a 2D displacement sensor such as those found in a wireless mouse, and others. The important aspect is to know the magnitude of the input for roll or articulation for comparison with the detected change in location caused by the rotation or articulation of the catheter 102.

While it can be expected that some rotation or articulation of the catheter 102 is not translated from the proximal end at which the drive mechanism 200 or other input device the catheter 102 may be provided with sufficient torsional stiffness such that there is as close to possible a one-to-one correspondence from input to movement of the catheter 102. However, even where there is a lag or a loss in translation, since the drive mechanism 200 provides a known input, the system 100, and particularly the computing device 122 or the a locating module 116 can look for the response at the distal end of the catheter 102 and compare it to the input. If the response does not correspond exactly, a further movement (e.g., roll or articulation) can be undertaken and as more and more data is collected the variation between input and output can be assessed and the application running on computing device 122 or locating module 116 can be updated to take this variation into account for the roll calculation.

In at least one embodiment, the UI 150 may provide prompts to the user to perform an articulation or a rotation of the catheter at points during the procedure. In particular, as the catheter 102 approaches the target 152, to confirm the orientation of the catheter 102 the UI may signal the user to rotate or articulate the catheter 102. The articulation or rotation, provides a change in position and orientation that can be used to determine the roll or the $6^{th}$ DOF of the catheter 102. If needed multiple changes in position and orientation can be employed to ensure that the catheter 102 is directed such that a tool extended from the catheter 102 will impact the target 152.

Figure 4:
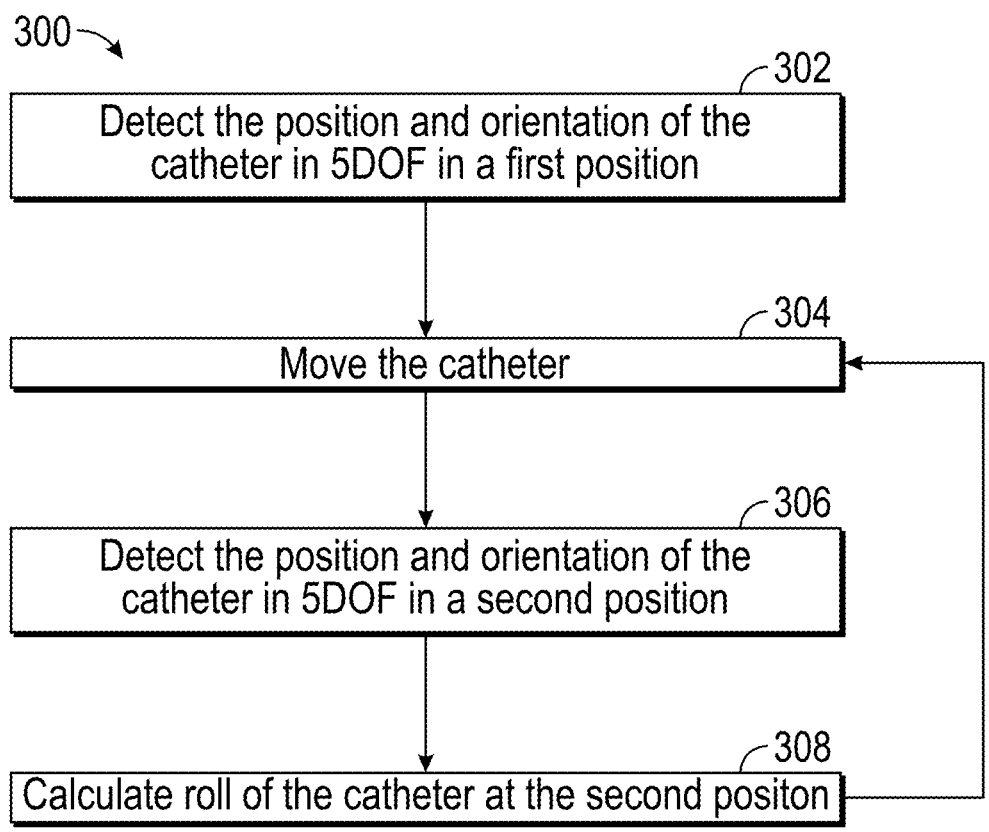
FIG. 4 is a method in accordance with the disclosure.

FIG. 4 depicts a method 300, which may be implemented in software operating on the computing device 122 or locating system 116. At step 302 the position and orientation of the distal portion of the catheter 102 is detected in 5DOF. At step 304 the catheter is moved. Step 304 may be an articulation of a straight catheter 102 or a roll of a curved catheter 102 as described above. At step 306 the position and orientation of the sensor 104 and therewith the distal portion of the catheter 102 is detected in 5DOF. At step 308, the change in position and orientation of the sensor 104 in 5DOF is used by the computing device 122 or locating system to calculate the amount of roll (i.e., the $6^{th}$ DOF) of the catheter 102. As noted above, the articulation or roll of the catheter 102 can be manually or automatically driven and may be repeated as frequently as necessary to accurately reflect the roll of the catheter 102 during navigation and particularly as the catheter 102 approaches the target 152.

Figure 5:
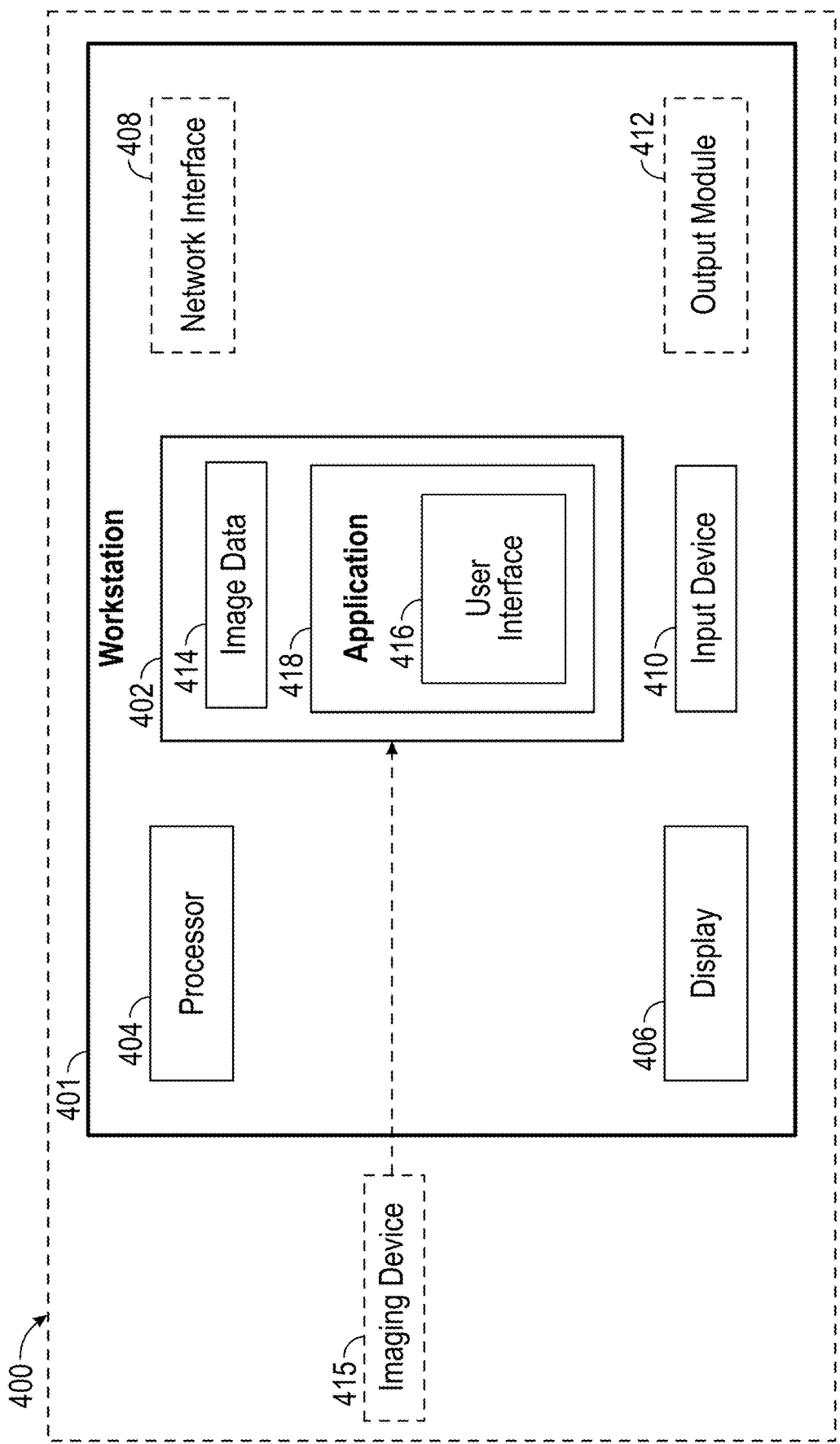
FIG. 5 is a schematic view of a computing device in accordance with aspects of the disclosure.

Reference is now made to FIG. 5, which is a schematic diagram of a system 400 configured for use with the methods of the disclosure including the method of FIG. 4. System 400 may include a workstation 401, and optionally a fluoroscopic imaging device or fluoroscope 415. In some embodiments, workstation 401 may be coupled with fluoroscope 415, directly or indirectly, e.g., by wireless communication. Workstation 401 may include a memory 402, a processor 404, a display 406 and an input device 410. Processor or hardware processor 404 may include one or more hardware processors. Workstation 401 may optionally include an output module 412 and a network interface 408. Memory 402 may store an application 418 and image data 414. Application 418 may include instructions executable by processor 404 for executing the methods of the disclosure including the method of FIG. 4.

Application 418 may further include a user interface 416. Image data 414 may include the CT scans, the generated fluoroscopic 3D reconstructions of the target area and/or any other fluoroscopic image data and/or the generated one or more slices of the 3D reconstruction. Processor 404 may be coupled with memory 402, display 406, input device 410, output module 412, network interface 408 and fluoroscope 415. Workstation 401 may be a stationary computing device, such as a personal computer, or a portable computing device such as a tablet computer. Workstation 401 may embed a plurality of computer devices.

Memory 402 may include any non-transitory computer-readable storage media for storing data and/or software including instructions that are executable by processor 404 and which control the operation of workstation 401 and, in some embodiments, may also control the operation of fluoroscope 415. Fluoroscope 415 may be used to capture a sequence of fluoroscopic images based on which the fluoroscopic 3D reconstruction is generated and to capture a live 2D fluoroscopic view according to this disclosure. In an embodiment, memory 402 may include one or more storage devices such as solid-state storage devices, e.g., flash memory chips. Alternatively, or in addition to the one or more solid-state storage devices, memory 402 may include one or more mass storage devices connected to the processor 404 through a mass storage controller (not shown) and a communications bus (not shown).

Although the description of computer-readable media contained herein refers to solid-state storage, it should be appreciated by those skilled in the art that computer-readable storage media can be any available media that can be accessed by the processor 404. That is, computer readable storage media may include non-transitory, volatile and non-volatile, removable and non-removable media implemented in any method or technology for storage of information such as computer-readable instructions, data structures, program modules or other data. For example, computer-readable storage media may include RAM, ROM, EPROM, EEPROM, flash memory or other solid-state memory technology, CD-ROM, DVD, Blu-Ray or other optical storage, magnetic cassettes, magnetic tape, magnetic disk storage or other magnetic storage devices, or any other medium which may be used to store the desired information, and which may be accessed by workstation 1001.

Application 418 may, when executed by processor 404, cause display 406 to present user interface 416. User interface 416 may be configured to present to the user a single screen including a three-dimensional (3D) view of a 3D model of a target from the perspective of a tip of a medical device, a live two-dimensional (2D) fluoroscopic view showing the medical device, and a target mark, which corresponds to the 3D model of the target, overlaid on the live 2D fluoroscopic view, as shown, for example, in FIG. 2. User interface 416 may be further configured to display the target mark in different colors depending on whether the medical device tip is aligned with the target in three dimensions. The user interface 416 may further provide prompts to a user to articulate the catheter 102 to enable a roll or $6^{th}$ DOF determination during navigation of the catheter in accordance with aspects of this disclosure.

Network interface 408 may be configured to connect to a network such as a local area network (LAN) consisting of a wired network and/or a wireless network, a wide area network (WAN), a wireless mobile network, a Bluetooth network, and/or the Internet. Network interface 408 may be used to connect between workstation 401 and fluoroscope 415. Network interface 408 may be also used to receive image data 414. Input device 410 may be any device by which a user may interact with workstation 401, such as, for example, a mouse, keyboard, foot pedal, touch screen, and/or voice interface. Output module 412 may include any connectivity port or bus, such as, for example, parallel ports, serial ports, universal serial busses (USB), or any other similar connectivity port known to those skilled in the art. From the foregoing and with reference to the various figures, those skilled in the art will appreciate that certain modifications can be made to the disclosure without departing from the scope of the disclosure.

Though described generally above, further details of the roll determination can be observed with respect to FIGS. 6A through 6D. In FIG. 6A the catheter 102 is in an unarticulated condition. The X, Y, Z coordinates of the unarticulated catheter 102 define a 3D vector $V_0$ coaxial of the unarticulated catheter 102 coaxial with and forward defined from the end of the catheter 102. As depicted in FIG. 6A, because the catheter 102 is in an unarticulated state, the vectors $\hat{z}$ and $V_0$ substantially correspond. The pull wire 602 is attached at a distal end of the catheter 102, for example using a pull ring 604. Upon actuation, the pull wire 602 is retracted proximally towards a handle (not shown) or drive mechanism as depicted in FIGS. 3A, 3B to achieve the shape of the catheter 102 as depicted in FIG. 6B. The pull wire 602 is connected to the pull ring 604 at a known point (e.g., at a known radial location on the end catheter 102) relative to the handle or drive mechanism and shaft of the catheter 101. The effect of retracting the pull wire, and specifically an expected change in position and orientation of the distal tip of the catheter 102 caused by a known amount of retraction of the pull wire 602 is also known. This data may be stored in a look-up table or other data storage means. However, due to the physiology of the lungs, a change in position due to a set amount of pull wire 602 retraction, may not result in the expected change in position.

During navigation, at any point an initial the 5DOF position and orientation of the sensor can be recorded (including the $X_0, Y_0, Z_0$ coordinates). To determine the roll of the catheter an input to pull wire 602 is required. This input causes an articulation of the catheter 102 and a change in position to move the distal portion of the catheter to position B as depicted in FIG. 6C. At position B coordinates $X_1, Y_1,$ and $Z_1$ define a new position of the distal portion of the catheter 102. $X_1, Y_1,$ and $Z_1$ also define a new vector $V_1$. Vectors $V_0$ and $V_1$ define a plane of articulation. A vector P, normal to the plane of articulation, which can be derived by the formula $P = V_0 \times V_1$ provides then a changing datapoint that can be used to approximation of the roll of the catheter 102. P is necessarily perpendicular to both original vector $V_0$ and $V_1$, by being perpendicular to the articulation plane defined by the two vectors. This vector can be compared to an expected vector P when the catheter 102 is unconstrained and with radial location of the pull wire relative to the handle and catheter shaft known. The difference between the expected vector P an the calculated vector P defines an approximation of the roll of the catheter 102.

As described herein above, by approximating the roll of the catheter 102, this data can be provided to the user via the user interface during navigation to assist the user in understanding the orientation of the catheter 102. Further, this articulation may be relatively small and at a frequency that is undetected by the user, but used by the system to continually update the displayed roll of the catheter 102. As will be appreciated, other means of using vector analysis or kinematics may also be employed without departing from the scope of the disclosure.

While detailed embodiments are disclosed herein, the disclosed embodiments are merely examples of the disclosure, which may be embodied in various forms and aspects. For example, embodiments of an electromagnetic navigation system, which incorporates the target overlay systems and methods, are disclosed herein; however, the target overlay systems and methods may be applied to other navigation or tracking systems or methods known to those skilled in the art. Therefore, specific structural and functional details disclosed herein are not to be interpreted as limiting, but merely as a basis for the claims and as a representative basis for teaching one skilled in the art to variously employ the disclosure in virtually any appropriately detailed structure.

We claim:

1. A catheter navigation system comprising:
    a flexible catheter configured for navigation within a patient, the catheter including a five degrees of freedom (5DOF) sensor;
    a drive mechanism including at least one pull wire configured to change a position and orientation of the flexible catheter;
    a computing device configured to detect a 5DOF position and orientation of the sensor, the computing device including a memory and a processor, the memory storing thereon a computer program that when executed by the processor cause the computing device to perform steps of:
        detecting the position and orientation of the catheter in 5DOF at a first location, the detected position and orientation at the first location defining a first vector;
        signaling the drive mechanism to move the catheter;
        detecting the position and orientation of the catheter in 5DOF at a second location, the detected position and orientation at the second location defining a second vector;
        defining a plane of articulation between the first and second vector;
        determining a third vector perpendicular to the plane of articulation;
        comparing the third vector to an expected third vector; and
        calculating a roll of the catheter at the second location, wherein the roll calculation resolves the detected position and orientation of a distal portion of the catheter at the second position and orientation in six degrees of freedom (6DOF).

2. The catheter navigation system of claim 1, wherein the catheter includes a lumen therethrough for insertion of a biopsy or treatment tool.

3. The catheter navigation system of claim 1, wherein the drive mechanism causes the catheter to articulate.

4. The catheter navigation system of claim 1, wherein the drive mechanism causes the catheter to rotate.

5. The catheter navigation system of claim 1, wherein the drive mechanism is a manual drive mechanism.

6. The catheter navigation system of claim 1, wherein the computing device is configured to display a user interface, the user interface depicting the 6DOF position and orientation of the catheter in relation to a target.

7. The catheter navigation system of claim 1, wherein the 5DOF sensor is an electromagnetic sensor.

8. The catheter navigation system of claim 1, wherein the 5DOF sensor is a shape sensor.

9. The catheter navigation system of claim 1, further comprising a fluoroscope, wherein the fluoroscope is configured for confirming the position and orientation of the catheter.

10. The catheter navigation system of claim 1, wherein signaling the drive mechanism to move the catheter occurs at a frequency between 3 Hz and 10 Hz.

11. A method for detecting a position and orientation of a catheter in six degrees of freedom (6DOF), the method comprising:
   detecting a position and orientation of the catheter in five degrees of freedom (5DOF) in a first location, the detected position and orientation at the first location defining a first vector;
   signaling a drive mechanism to move the catheter;
   detecting a position and orientation of the catheter in 5DOF in a second location, the detected position and orientation at the second location defining a second vector;
   defining a plane of articulation between the first and second vector;
   determining a third vector perpendicular to the plane of articulation;
   comparing the third vector to an expected third vector; and
   calculating a roll of the catheter at the second location based on a difference between the third vector and the expected third vector wherein the calculated roll resolves the detected position and orientation of a distal portion of the catheter at the second location in 6DOF.

12. The method of claim 11, further comprising articulating the catheter with the drive mechanism.

13. The method of claim 11 further comprising rotating the catheter, wherein the catheter is curved.

14. The method of claim 11, wherein the position of the catheter is detected via an electromagnetic sensor positioned in the distal portion of the catheter.

15. The method of claim 11, wherein the position of the catheter is detected via a shape sensor positioned in the distal portion of the catheter.

16. The method of claim 11, further comprising displaying on a computing device a user interface, the user interface depicting the 6DOF position and orientation of the catheter in relation to a target.

17. The method of claim 11, wherein signaling the drive mechanism to move the catheter occurs at a frequency between 3 Hz and 10 Hz.

18. A method for detecting a position and orientation of a catheter in six degrees of freedom (6DOF), the method comprising:
   detecting X, Y, Z, pitch and yaw position and orientation of a sensor on a distal portion of a catheter at a first position, and defining a first vector;
   detecting X, Y, Z, pitch and yaw position and orientation of the sensor on the distal portion of the catheter at a second position, and defining a second vector;
   defining a plane of articulation between the first and second vector;
   determining a third vector perpendicular to the plane of articulation;
   comparing the third vector to an expected third vector; and
   calculating a roll orientation of the sensor at the second position based on a difference between the third vector and the expected third vector wherein the calculated roll orientation resolves the detected position and orientation of the distal portion of the catheter at the second position in 6DOF.

19. The method of claim 18 wherein a pull wire moves the catheter from the first position to the second position.

20. The method of claim 19, wherein a drive mechanism operating at between 3 Hz and 10 Hz actuates the pull wire to move the catheter from the first position to the second position.

* * * * *